United States Patent
Pan

(10) Patent No.: US 9,546,961 B1
(45) Date of Patent: Jan. 17, 2017

(54) METHOD OF RAPID IDENTIFICATION OF NATURAL AND SYNTHETIC DIAMONDS USING THIRD-ORDER RAMAN SPECTRA

(71) Applicant: Dong-Shyogn Pan, Taipei (TW)

(72) Inventor: Dong-Shyogn Pan, Taipei (TW)

( * ) Notice: Subject to any disclaimer, the term of this patent is extended or adjusted under 35 U.S.C. 154(b) by 0 days.

(21) Appl. No.: 15/083,305

(22) Filed: Mar. 29, 2016

(51) Int. Cl.
   - *G01N 21/00* (2006.01)
   - *G01N 21/87* (2006.01)
   - *G01N 21/65* (2006.01)

(52) U.S. Cl.
   CPC .............. *G01N 21/87* (2013.01); *G01N 21/65* (2013.01)

(58) Field of Classification Search
   CPC ........ G01N 21/64; G01N 21/65; G01N 21/87; G01N 21/8806; G01N 33/381
   See application file for complete search history.

(56) References Cited

U.S. PATENT DOCUMENTS 5,835,200 A * 11/1998 Smith .................... G01N 21/87
356/30

* cited by examiner

*Primary Examiner* — Abdullahi Nur

(57) ABSTRACT

The method of rapid identification of natural and synthetic diamonds using a third-order Raman spectra is to make a diamond third order under large-scale comparative studies with synthetic diamond (CVD & HPHT) to distinguish natural and synthetic diamonds with their differences in Raman peaks. This analysis of the differences in characteristic peak phenomenon can form the basis of a rapid identification and analytical technique.

4 Claims, 22 Drawing Sheets

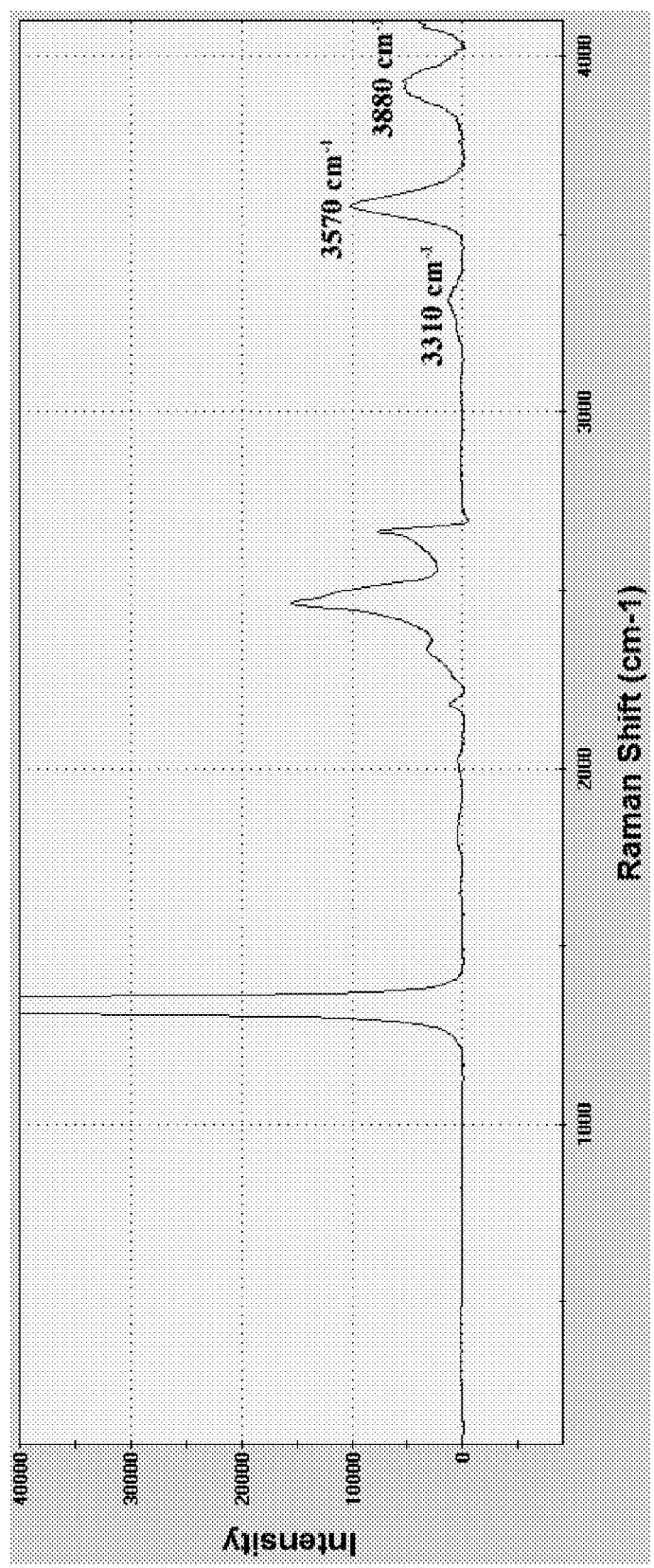
FIG. 2a-A

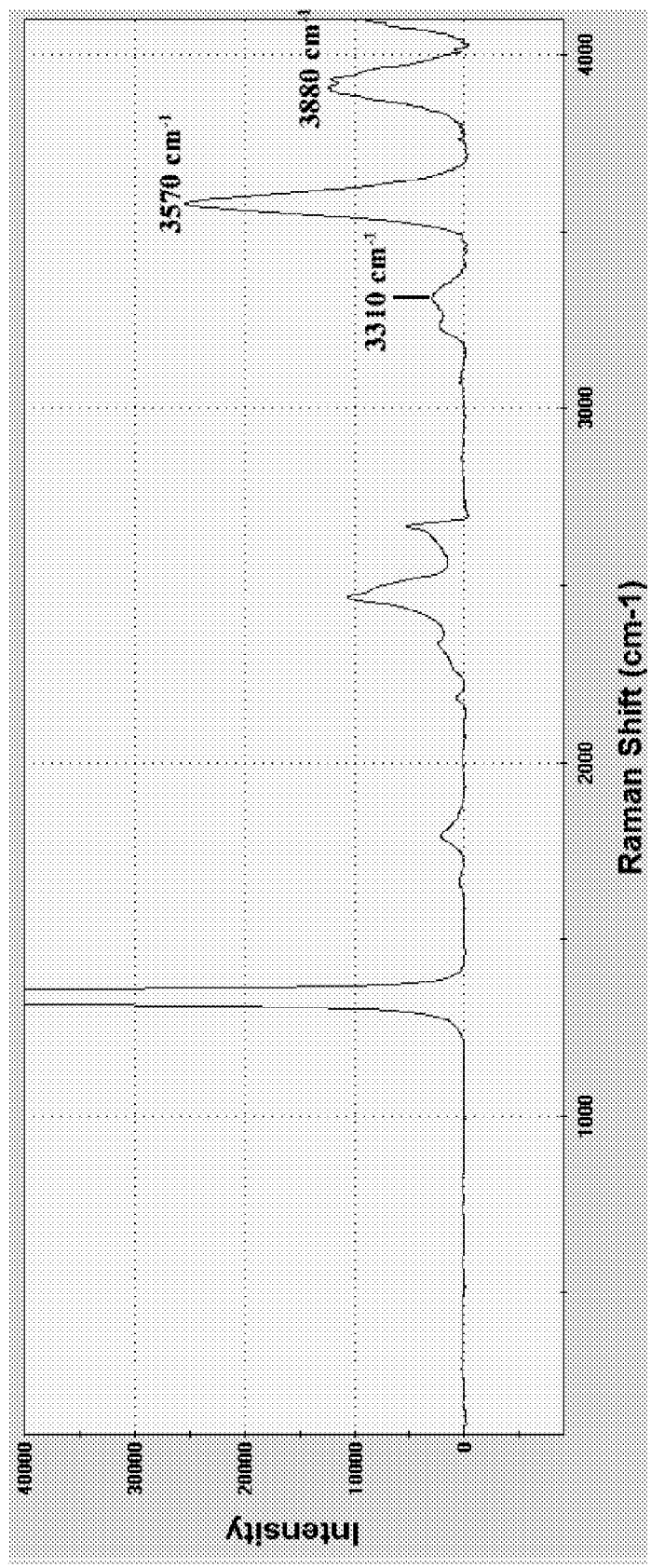
FIG. 2a-B

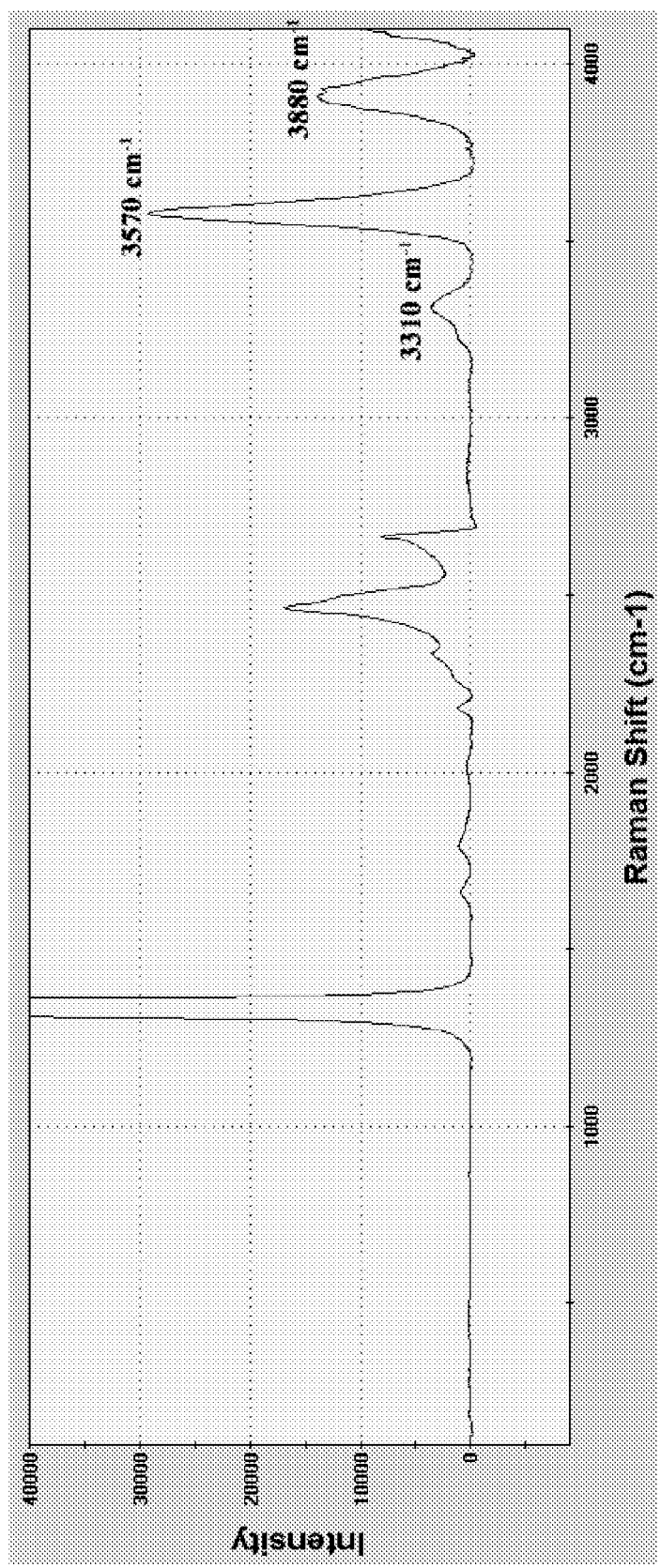
FIG. 2a-C

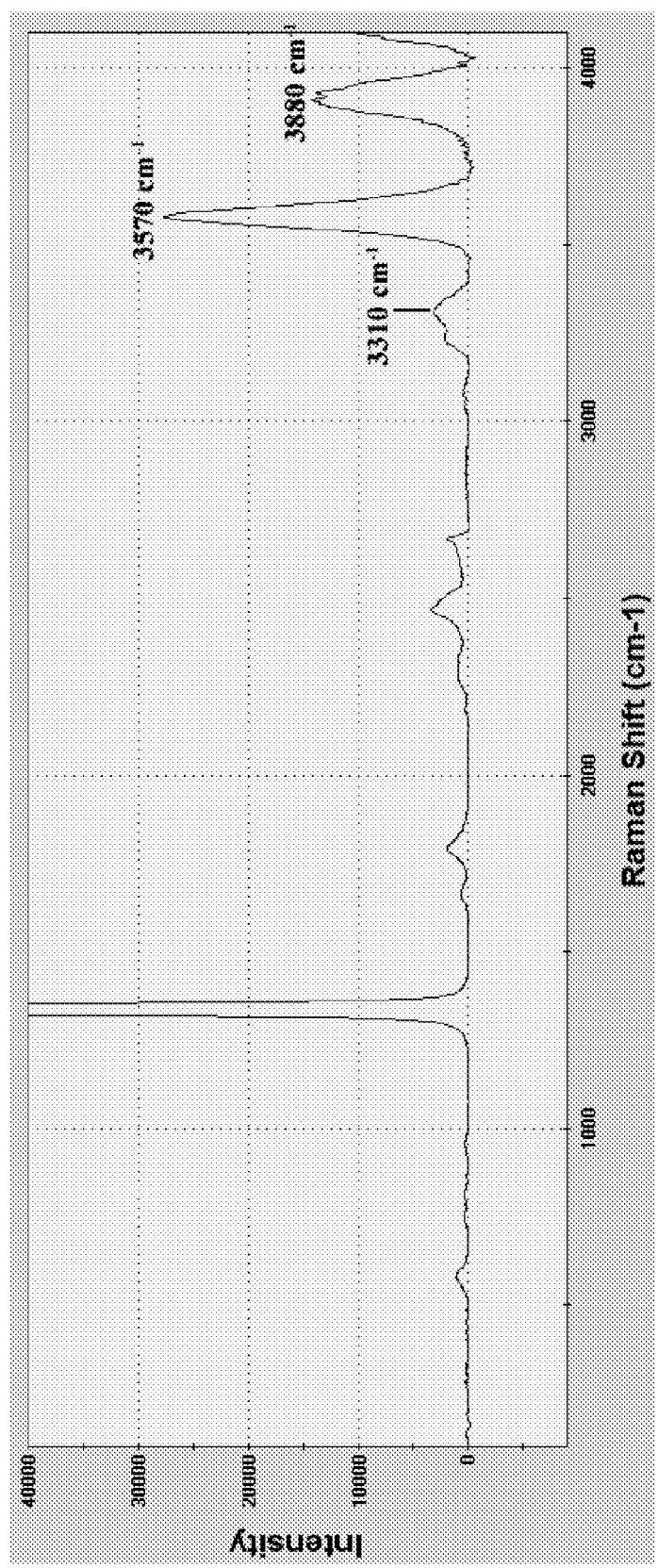
FIG. 2a-D

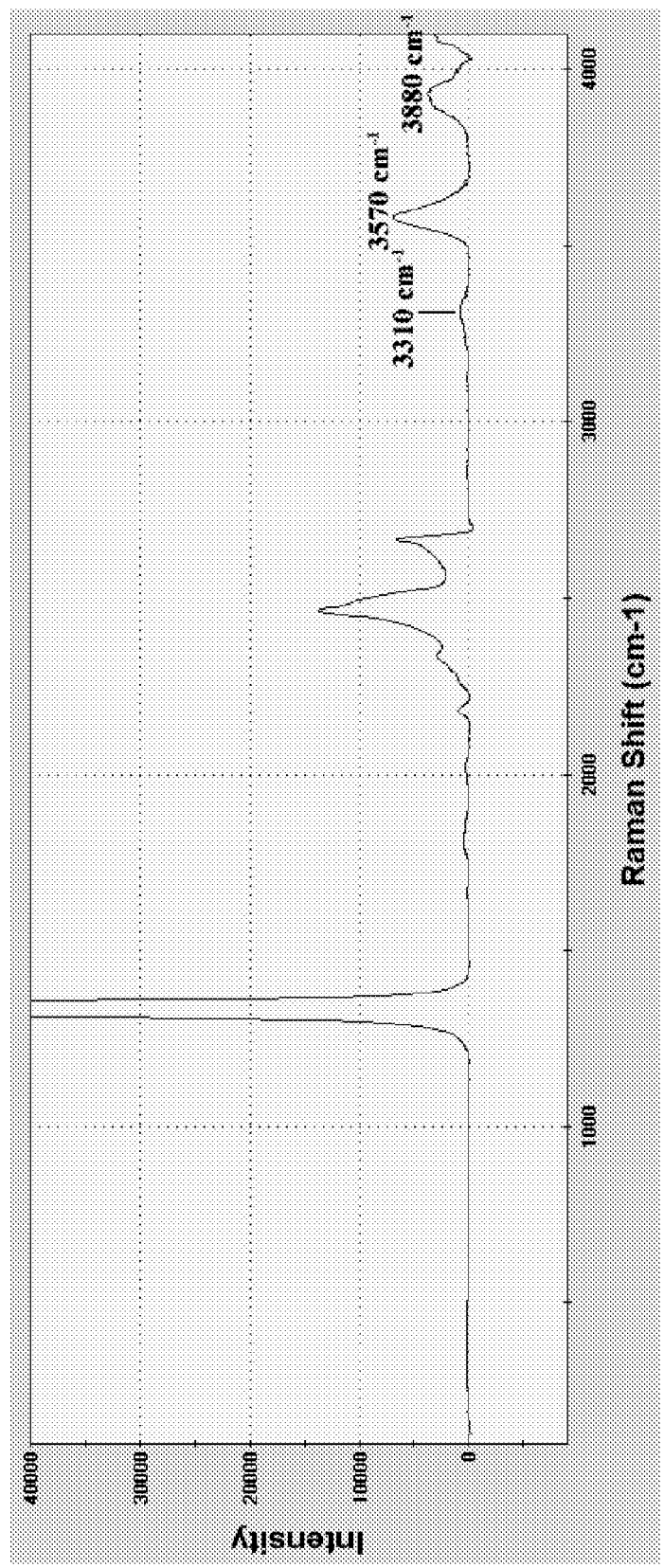
FIG. 2a-E

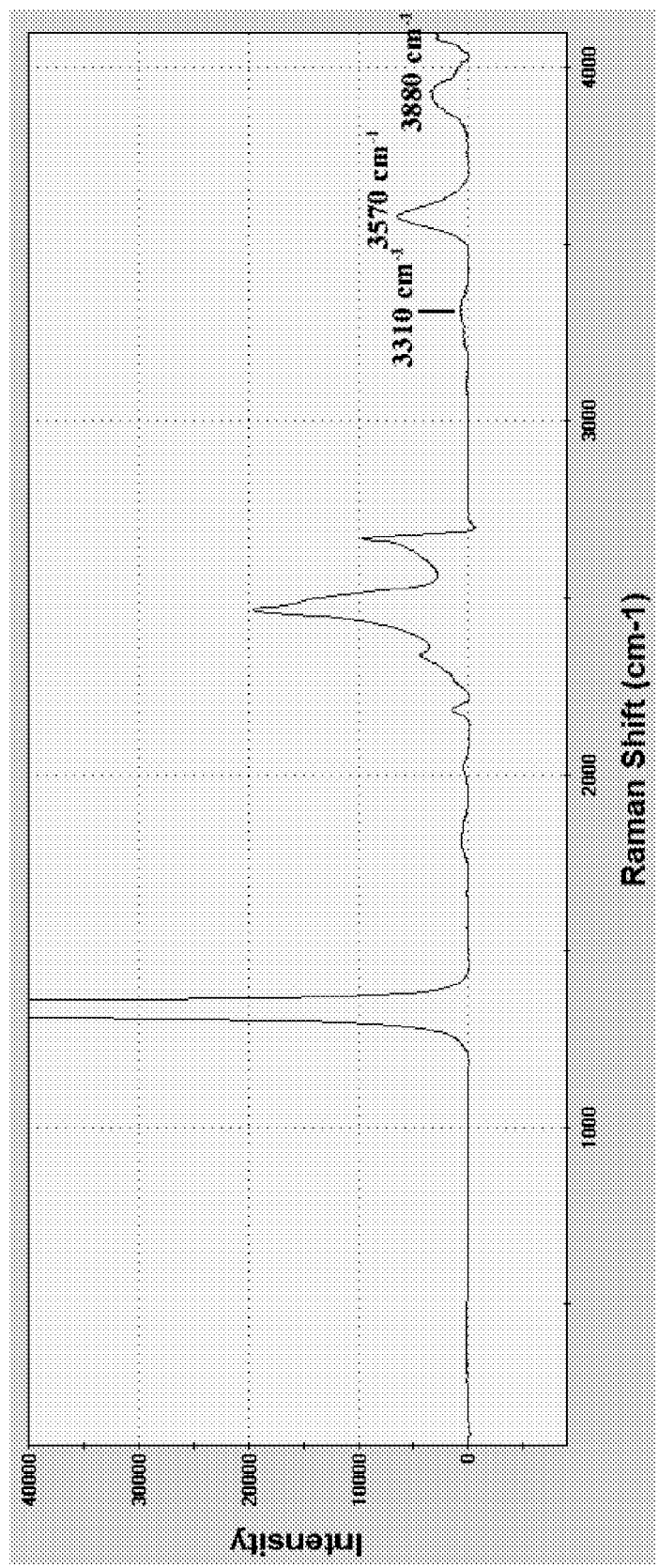
FIG. 2a-F

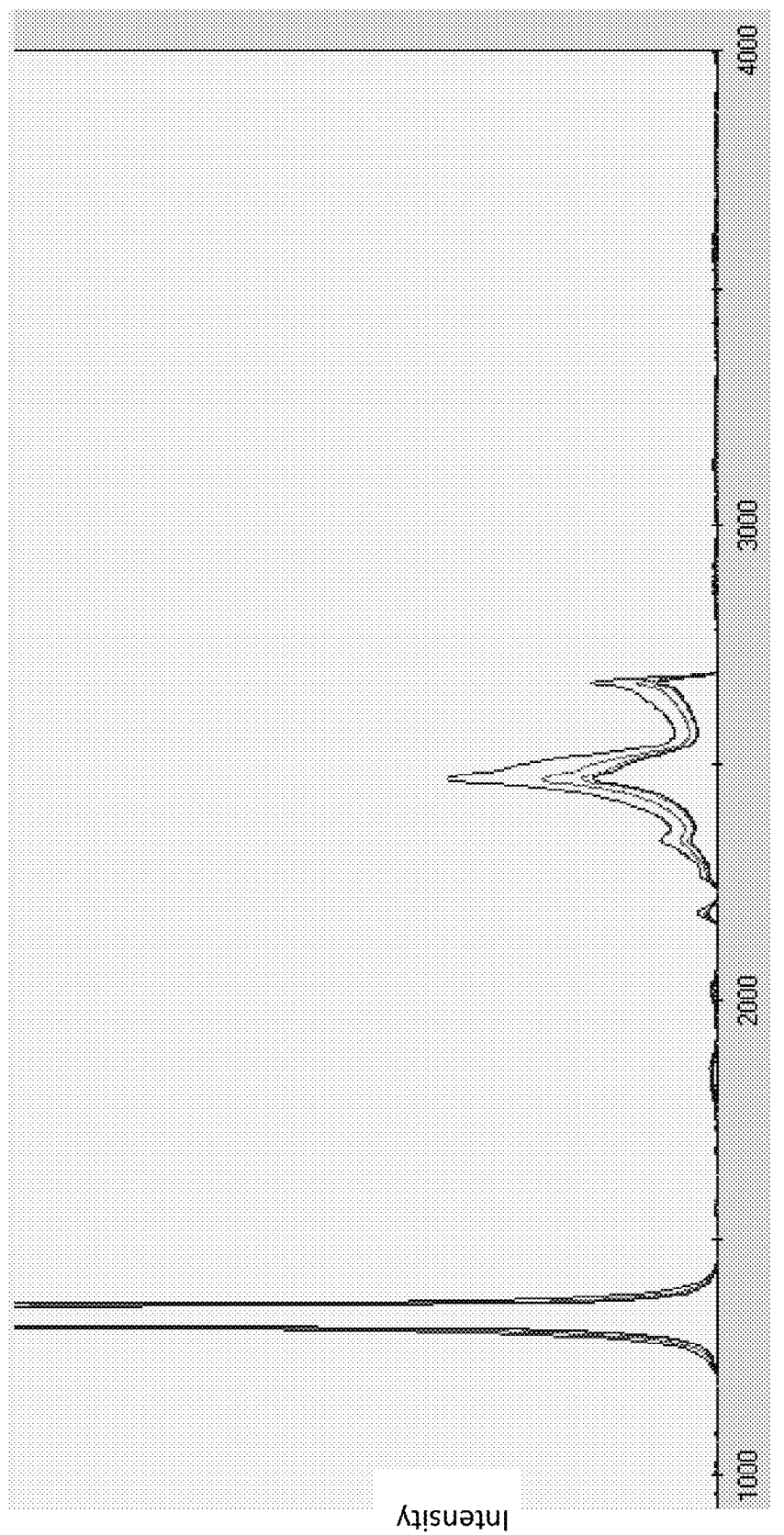

METHOD OF RAPID IDENTIFICATION OF NATURAL AND SYNTHETIC DIAMONDS USING THIRD-ORDER RAMAN SPECTRA

BACKGROUND OF THE INVENTION

1. Field of the Invention

The present invention relates to a method for identifying natural and synthetic diamonds, and particularly to a method of rapid identification of natural and synthetic diamonds using a third-order Raman spectra.

2. Related Art

Raman spectroscopy is used as a diagnostic tool for diamonds because each carbon allotrope displays a clearly identifiable Raman signature, it is non-destructive, requires little or no specimen preparation. Raman scattering from diamond has been disclosed by prior literatures, which describe the fundamental properties of the Raman spectra of natural and synthetic diamonds. Most natural untreated diamonds exhibit nitrogen-vacancy crystallographic defects and exhibit a series of typical second and third order Raman peaks as shown in FIG. 1. Crystallographic defects causing the Raman peaks for natural untreated diamonds are not fully understood. Therefore, it is a pressing issue to find out a method for rapidly identifying natural and synthetic diamonds through the existing Raman technique.

SUMMARY OF THE INVENTION

Accordingly, an object of the present invention is to provide a method of rapid identification of natural and synthetic diamonds using a third-order Raman spectra.

To achieve the above-mentioned object, the method comprises steps of: providing a Raman analyzer operating with a laser power at 50 mW, a laser beam of wavelength 532 nm, and spectral collection time of 0.1 seconds at an average of 20 times, for an average detection of surfaces of diamonds; utilizing a large spot scanning probe for sample screening and obtaining wave number and intensity of the diamonds; the wave number and intensity being automatically corrected via a software and a background fluorescence being masked automatically; a spectral range of the Raman analyzer used for data acquisition set to be 100-4200 $cm^{-1}$ in order to facilitate a Raman spectrum with the correct strength and a flat baseline; and the spectrum being further normalized to identify treated samples with a third-order spectrum.

BRIEF DESCRIPTION OF THE DRAWINGS

FIGS. 2a-A to 2a-F respectively show Raman spectra (A~F) of natural untreated Ia and IIa diamonds;

FIG. 2b shows overlaid Raman spectra of DGA 01~32 natural untreated Ia and IIa diamonds;

FIG. 2c shows overlaid Raman spectra of DGA 33~64 natural untreated Ia and IIa diamonds;

FIG. 3-1 shows overlaid Raman spectra of synthetic CVD diamond A~D;

FIG. 4-1 shows overlaid Raman spectra of synthetic HPHT diamond A~D;

FIG. 5-1 shows overlaid Raman spectra of natural diamond A & E (3310, 3570, 3880 $cm^{-1}$) and CVD diamond A & B (3122, 3622 $cm^{-1}$);

FIG. 5-2 shows overlaid Raman spectra of natural diamond A & E (3310, 3570, 3880 $cm^{-1}$) and HPHT diamond A & B.

DESCRIPTION OF THE PREFERRED EMBODIMENTS

A method of rapid identification of natural and synthetic diamonds using a third-order Raman spectra is to utilize Toptek-Enwave (TSI) G5 Raman analyzers, laser power at 50 mW, with spectral collection time of 0.1 seconds at an average of 20 times. It has a S/N>16,000, denoting its high sensitivity, and a large spot scanning probe (>100 um) for sample screening. The wave number and intensity is corrected automatically via dedicated software (Auto XY Calibration) and the background fluorescence is masked automatically (Auto-baseline). In order to facilitate the Raman spectrum, range is set with the correct strength and a flat baseline (100~4200 cm-1), the spectrum is further normalized to identify the treated samples with the third-order spectrum.

In this preferable embodiment, the method of the present invention covers over a hundred type Ia natural and synthetic samples under 532 nm Raman Analyzer for individual testing. For illustration, the results from 6 units of natural diamonds (FIGS. 2a-A, to 2a-F, A~F), 4 units of CVDs samples (FIGS. 3a to 3d, A~D), and 4 units of HPHT samples (FIGS. 4a to 4d, A~D) have been taken. Their Raman response is then matched with wave number and overlaid for analysis (FIGS. 2b~2c, FIG. 3-1, and FIG. 4-1).

Figure 1:
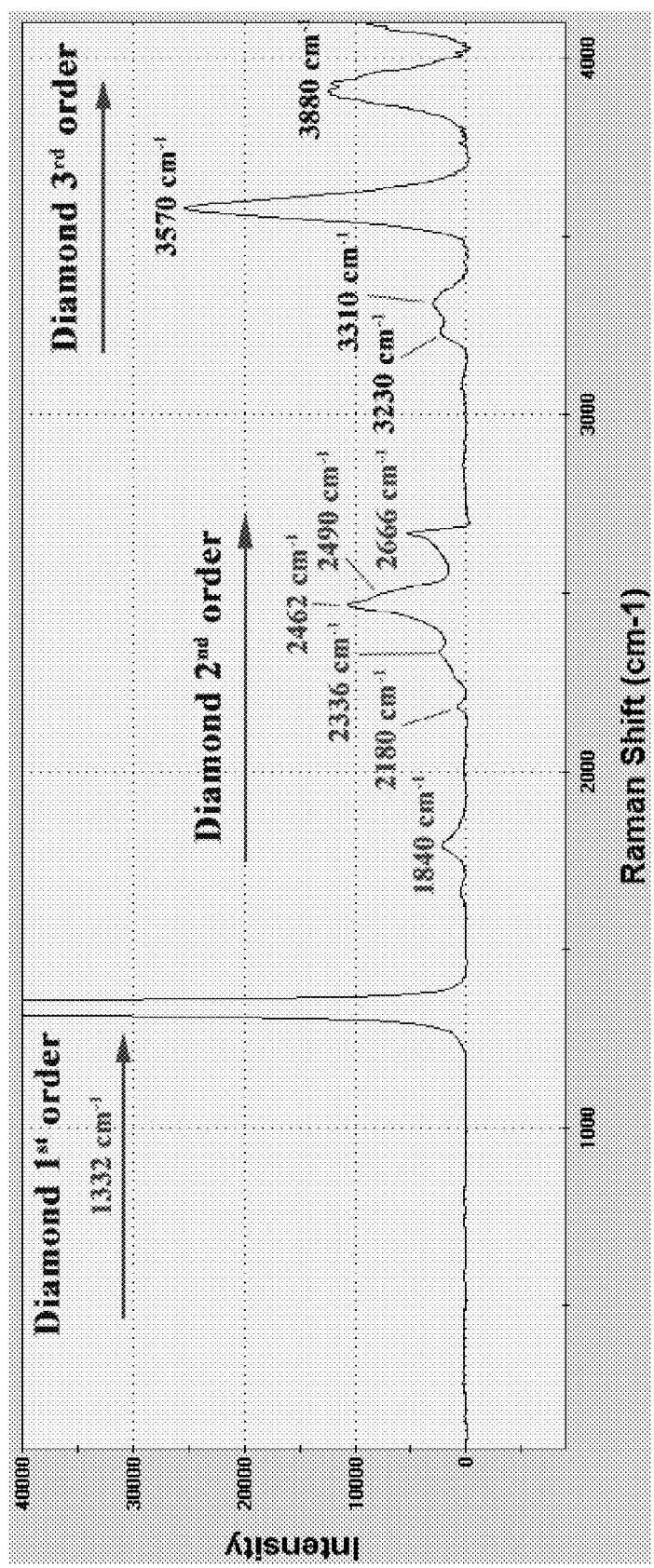
FIG. 1 shows Raman diamond $1^{st}$ order, diamond $2^{nd}$ order, and diamond $3^{rd}$ order spectra.
Figure 2B:
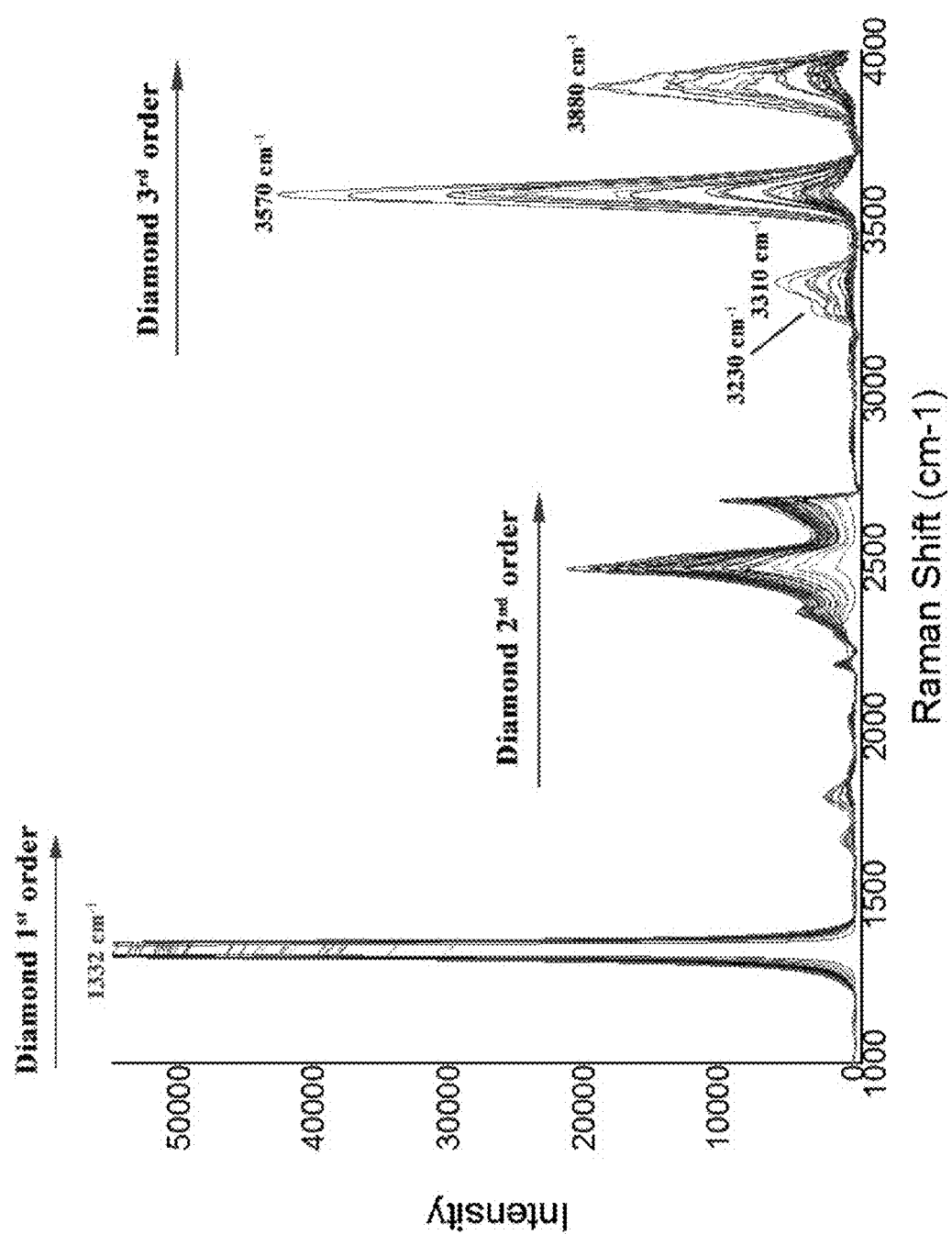
Figure 2C:
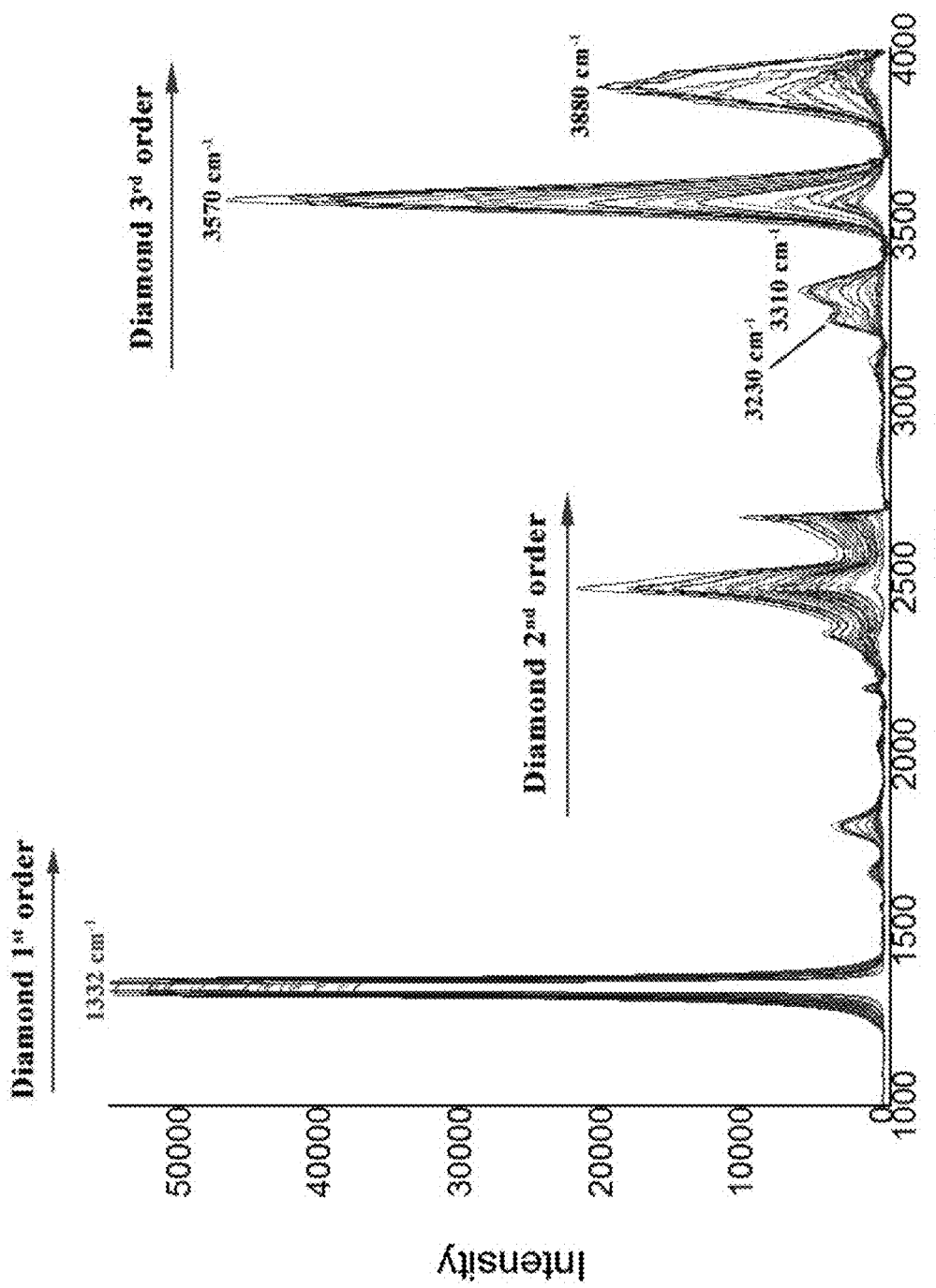
Figure 3A:
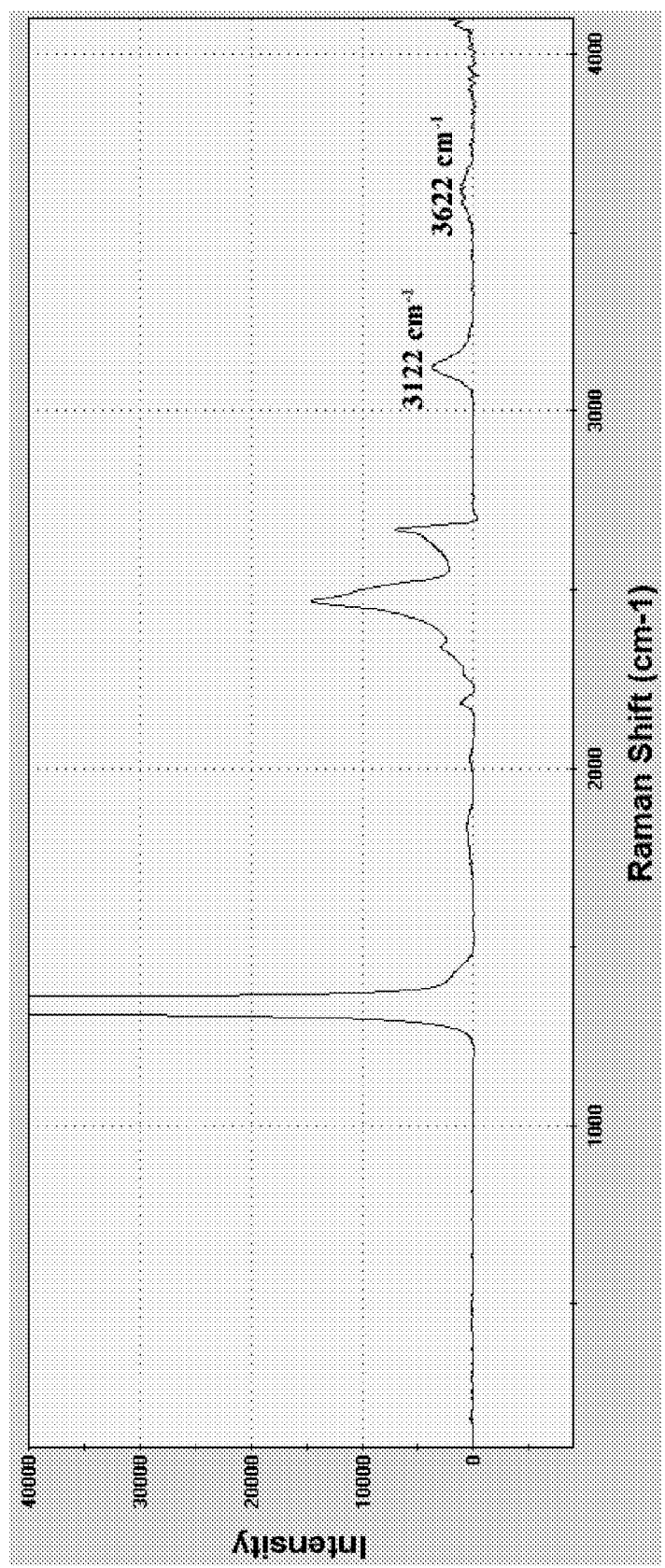
FIGS. 3a to 3d show Raman spectra of CVD diamond A~D.
Figure 3B:
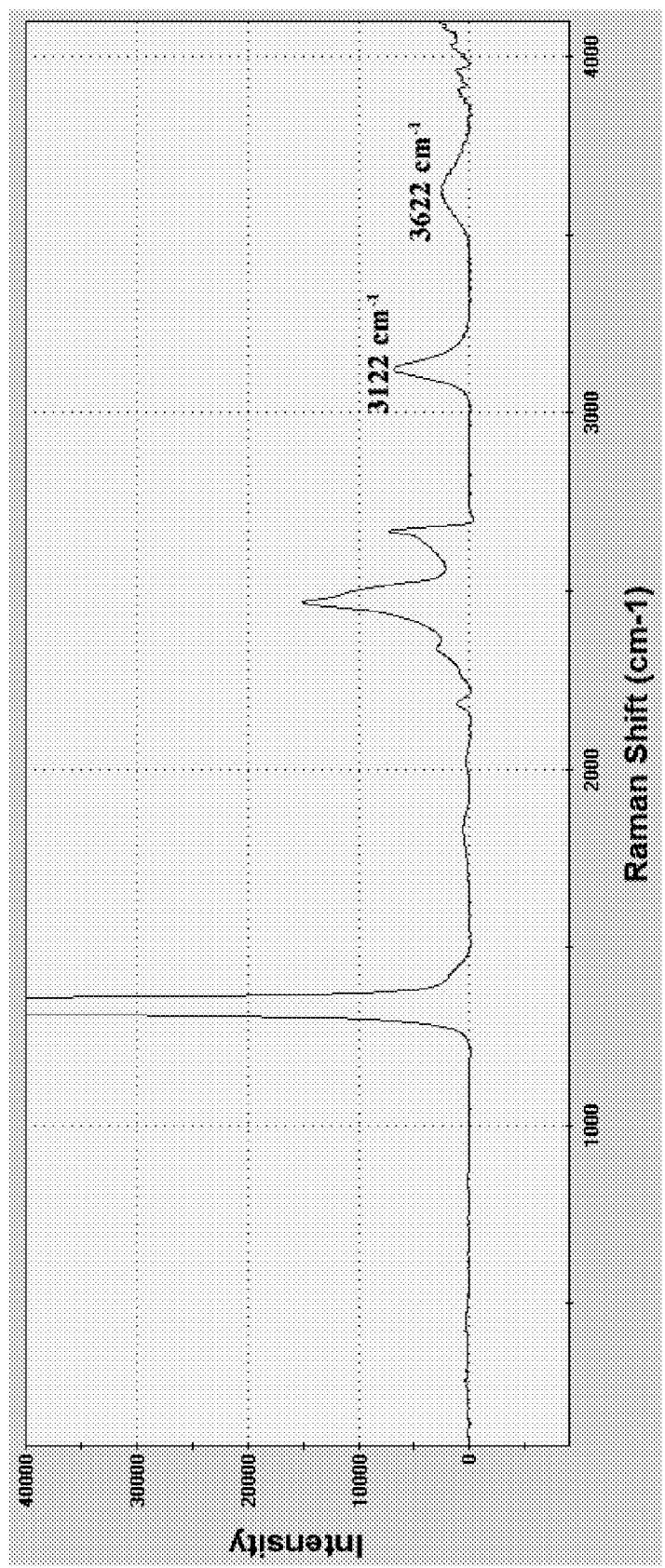
Figure 3C:
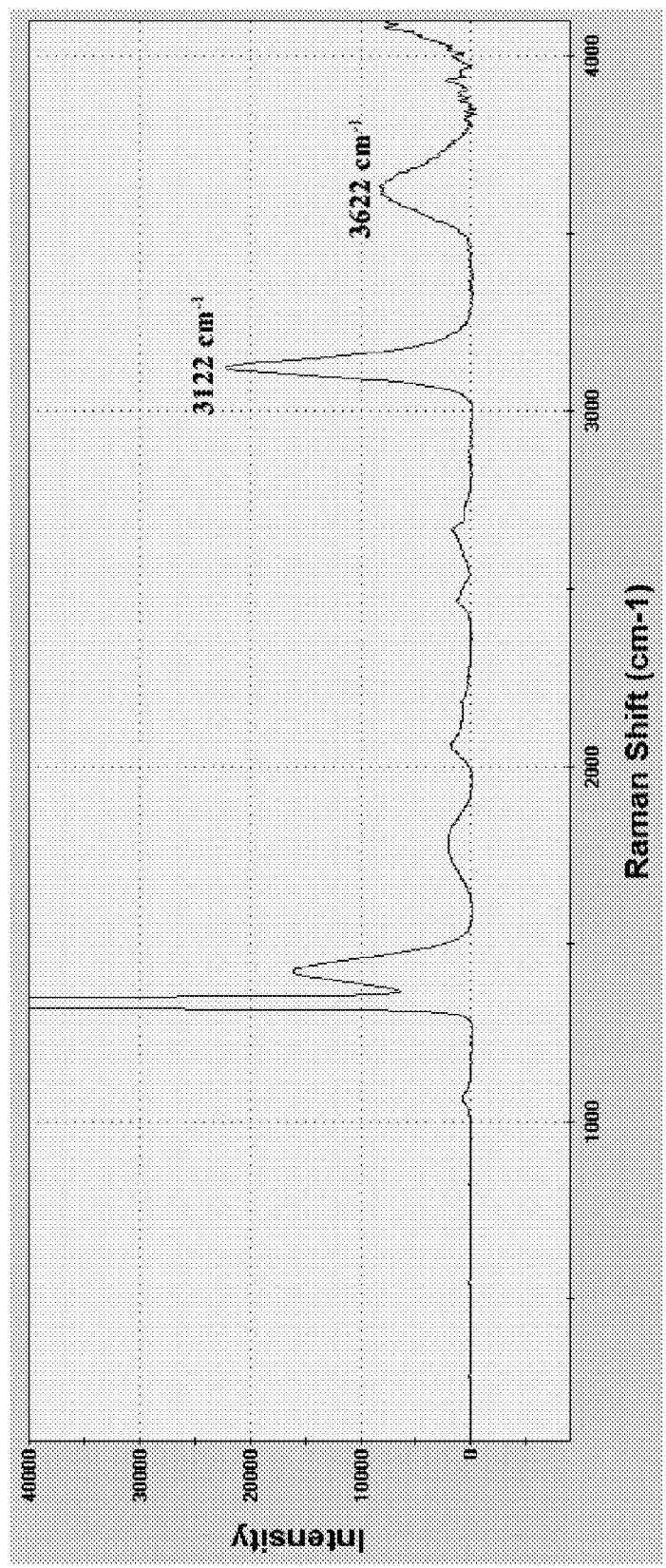
Figure 3D:
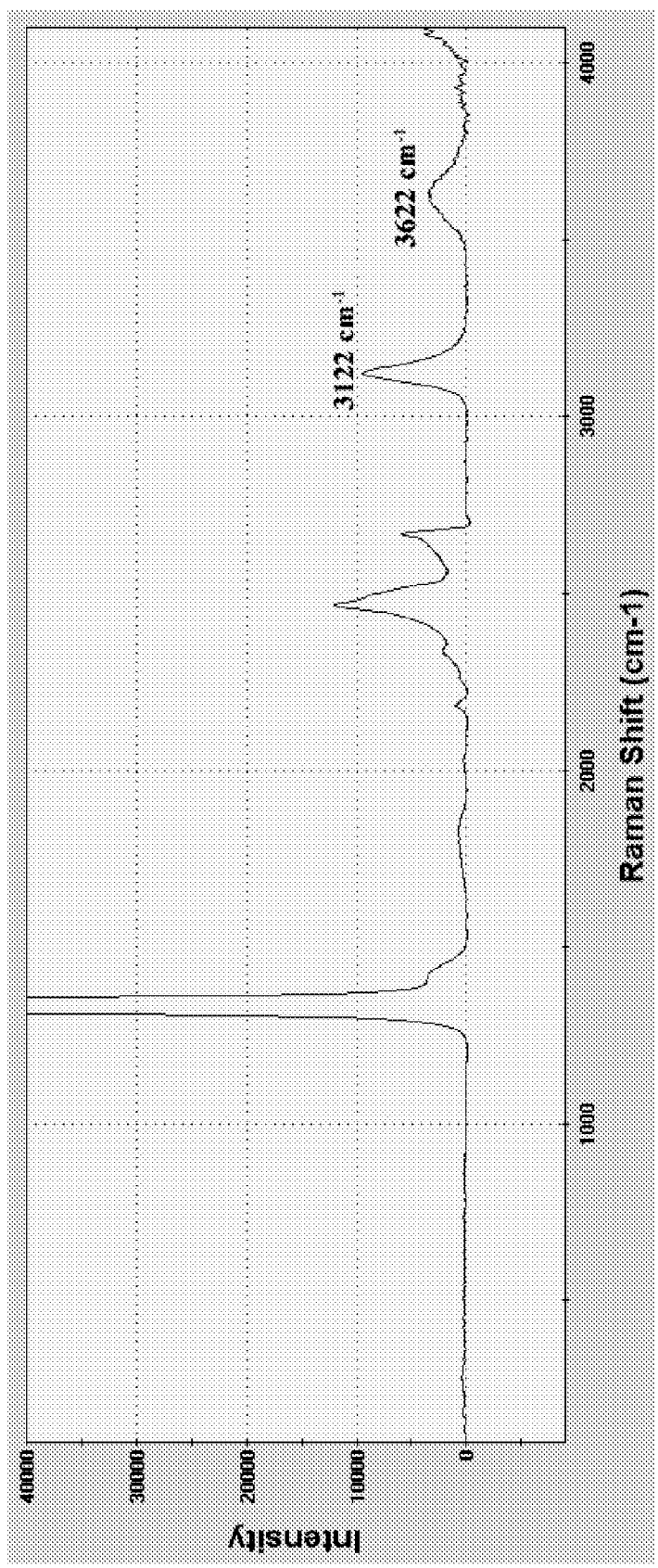
Figures 1, 3:
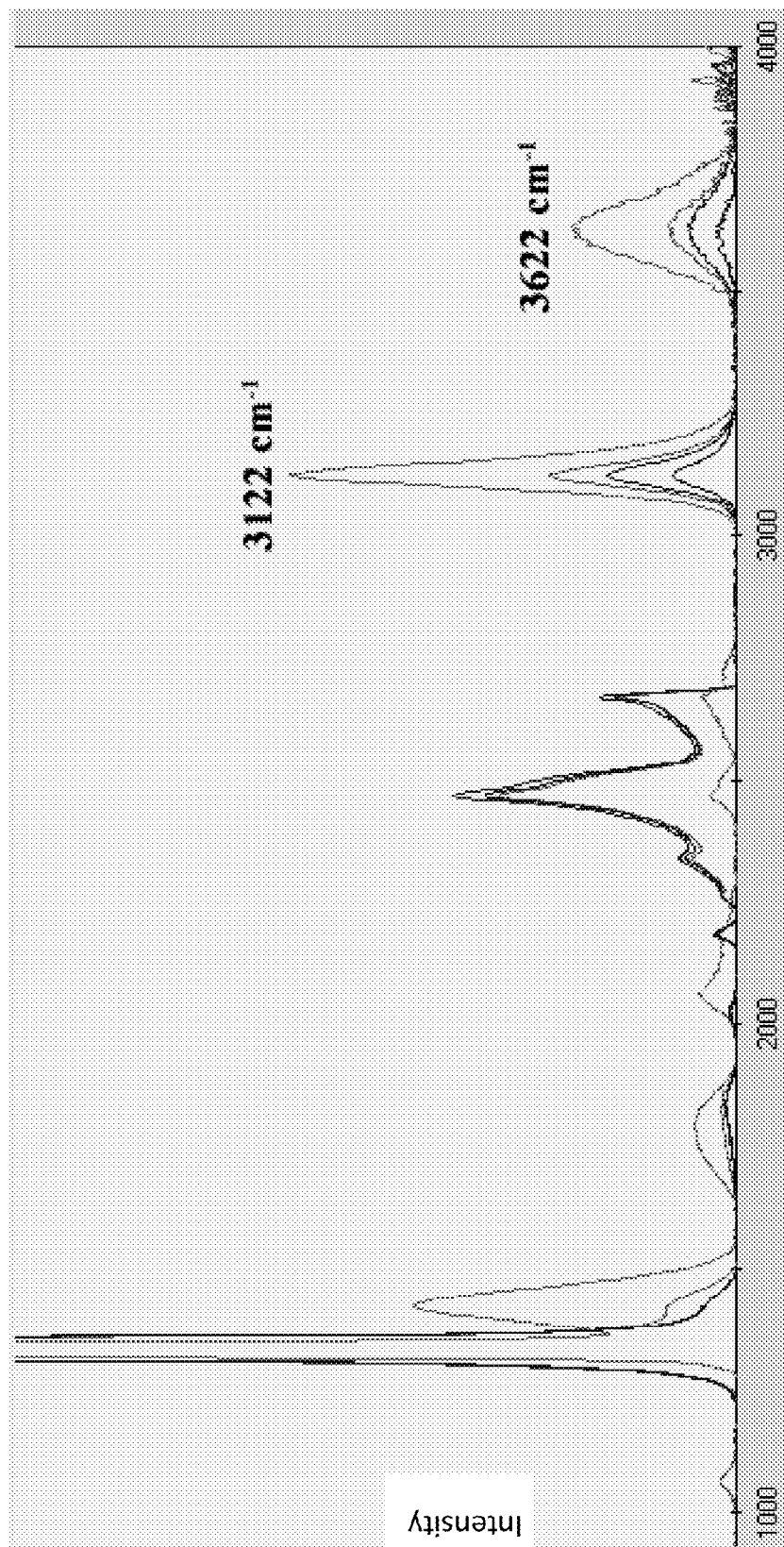
Figure 4A:
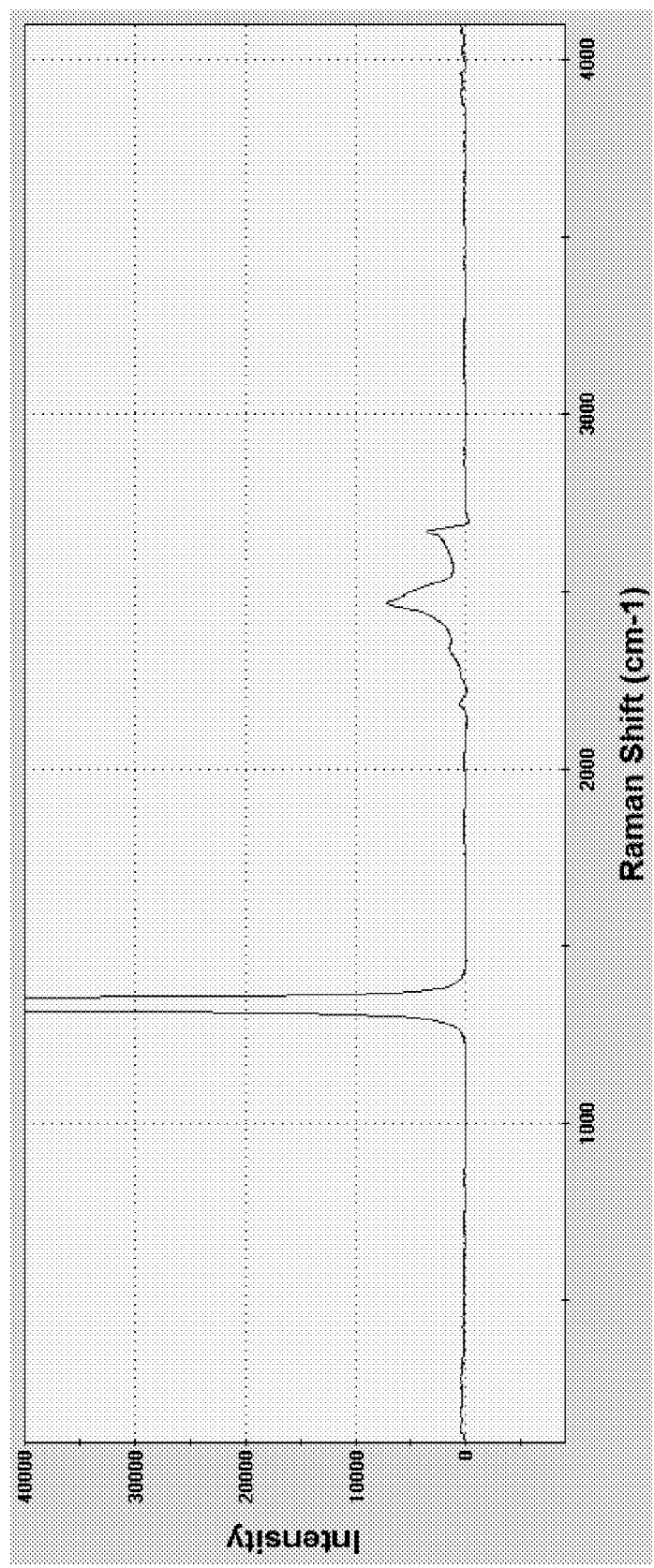
FIGS. 4a to 4d show Raman spectra of HPHT diamond A~D.
Figure 4B:
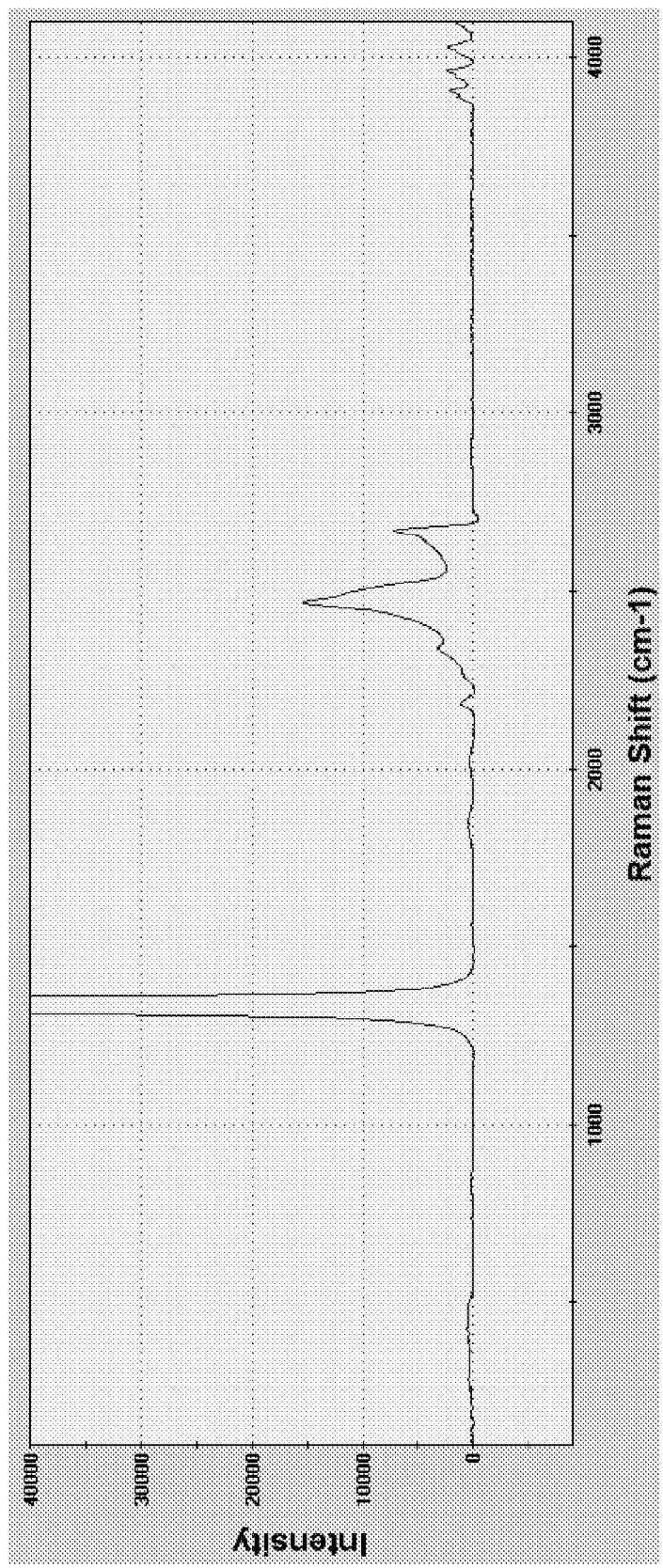
Figure 4C:
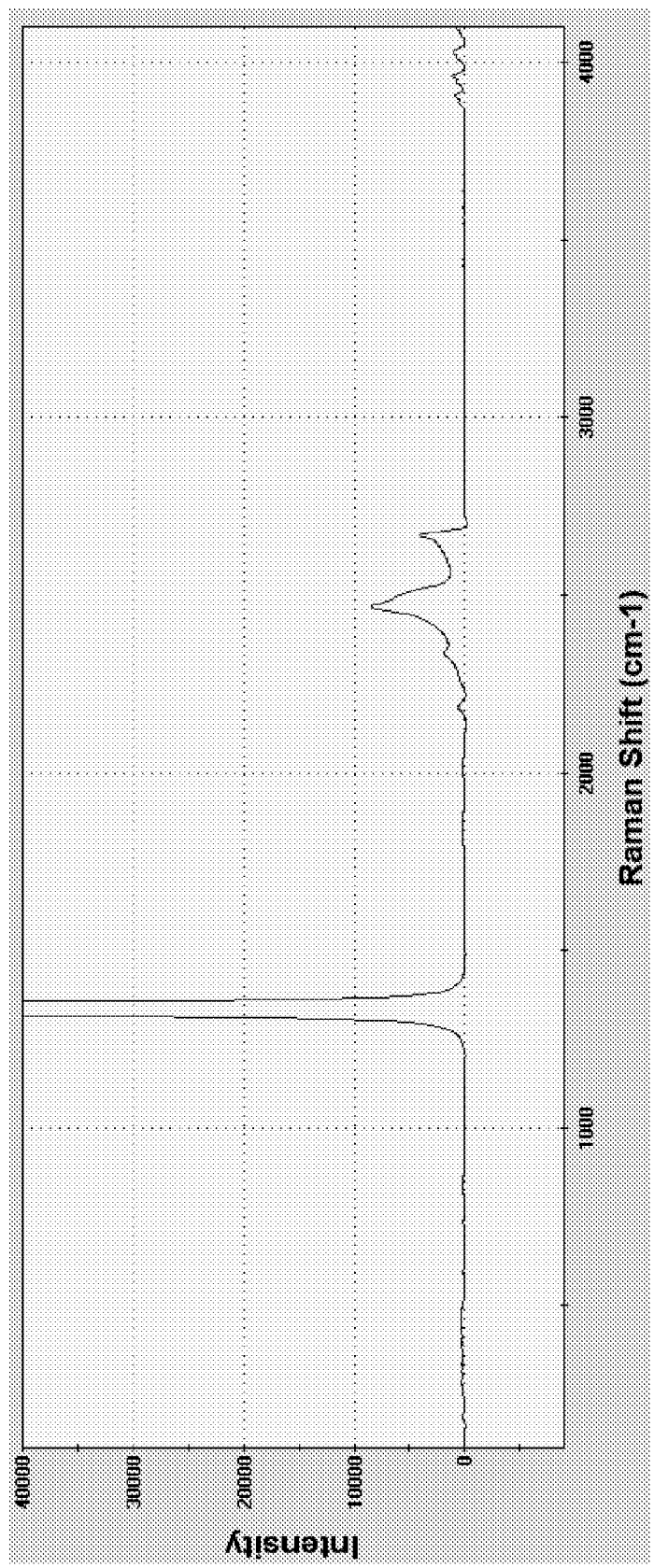
Figure 4D:
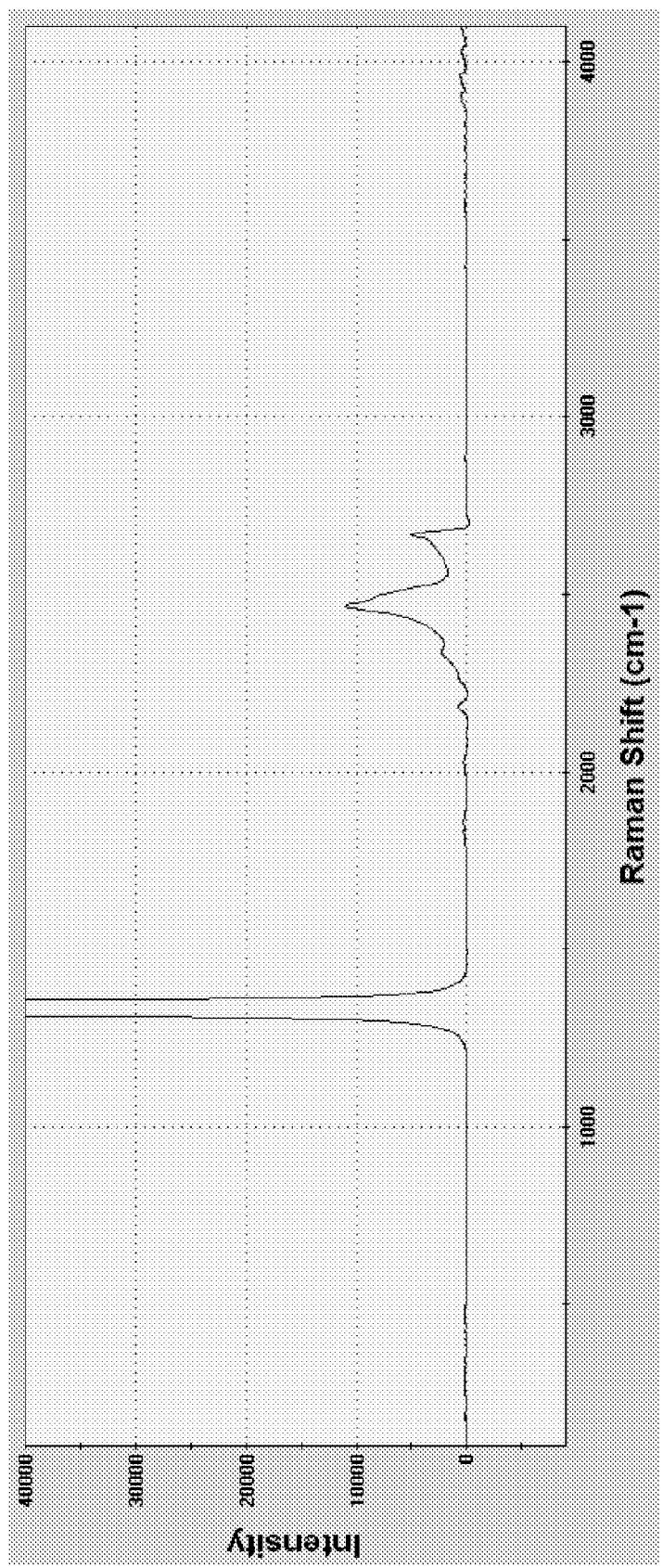

The method is to overlay the 64 natural diamonds spectra for analysis. It is found that the spectra has interrelation between 3000~4000 $cm^{-1}$ wave number of the third-order spectrum positioned at 3310 $cm^{-1}$, 3570 $cm^{-1}$, and 3880 $cm^{-1}$ as the three main Raman peaks (see FIGS. 2b and 2c); whereas the CVD only exhibits two fluorescence peaks close at 3120 $cm^{-1}$ and 3620 $cm^{-1}$ (as shown in FIG. 3-1); HPHT synthetic diamond, in comparison, does not carry any fluorescent or Raman peaks (see FIG. 4-1).

Figures 1, 5:
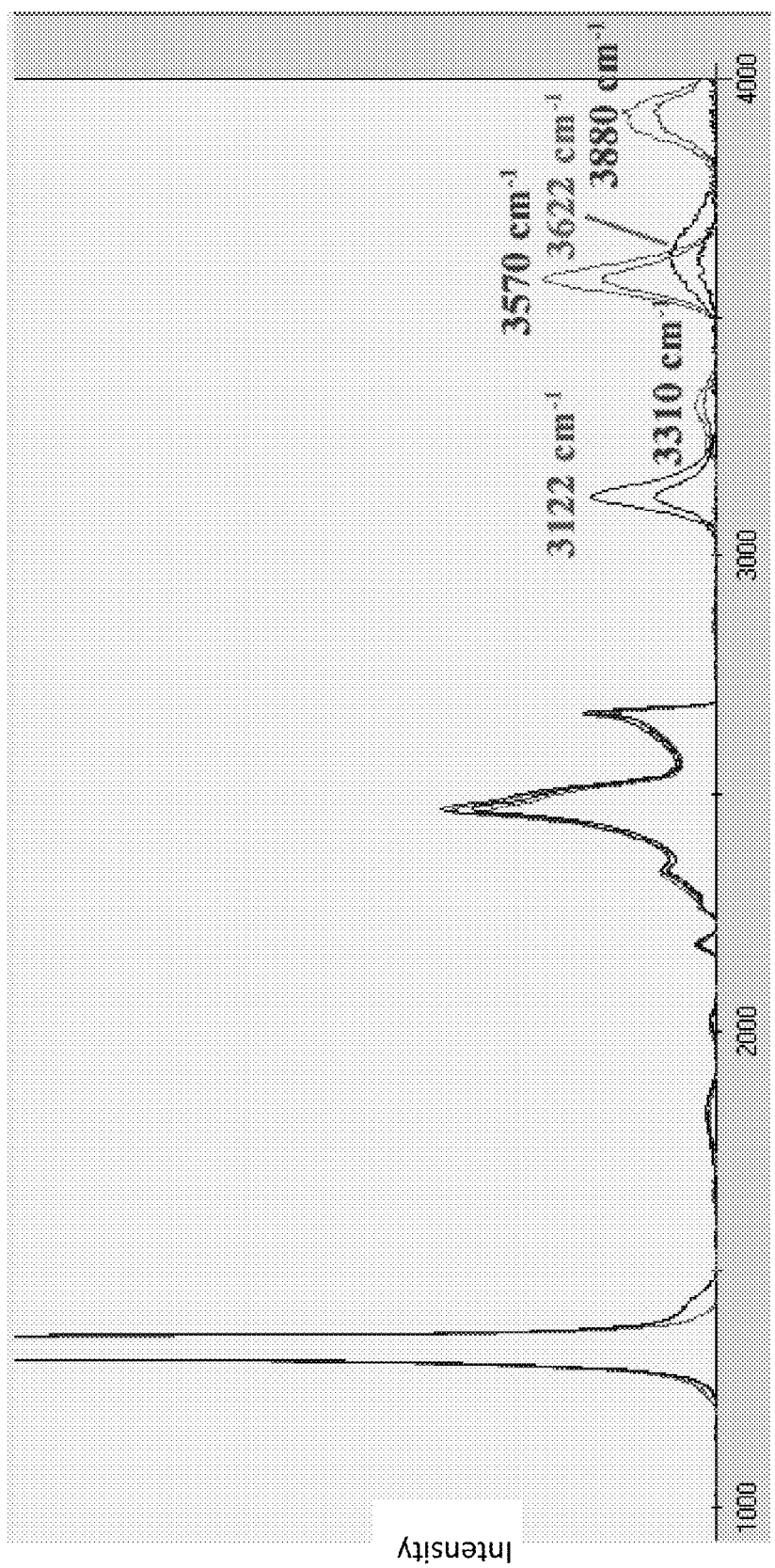
Figures 2, 5:
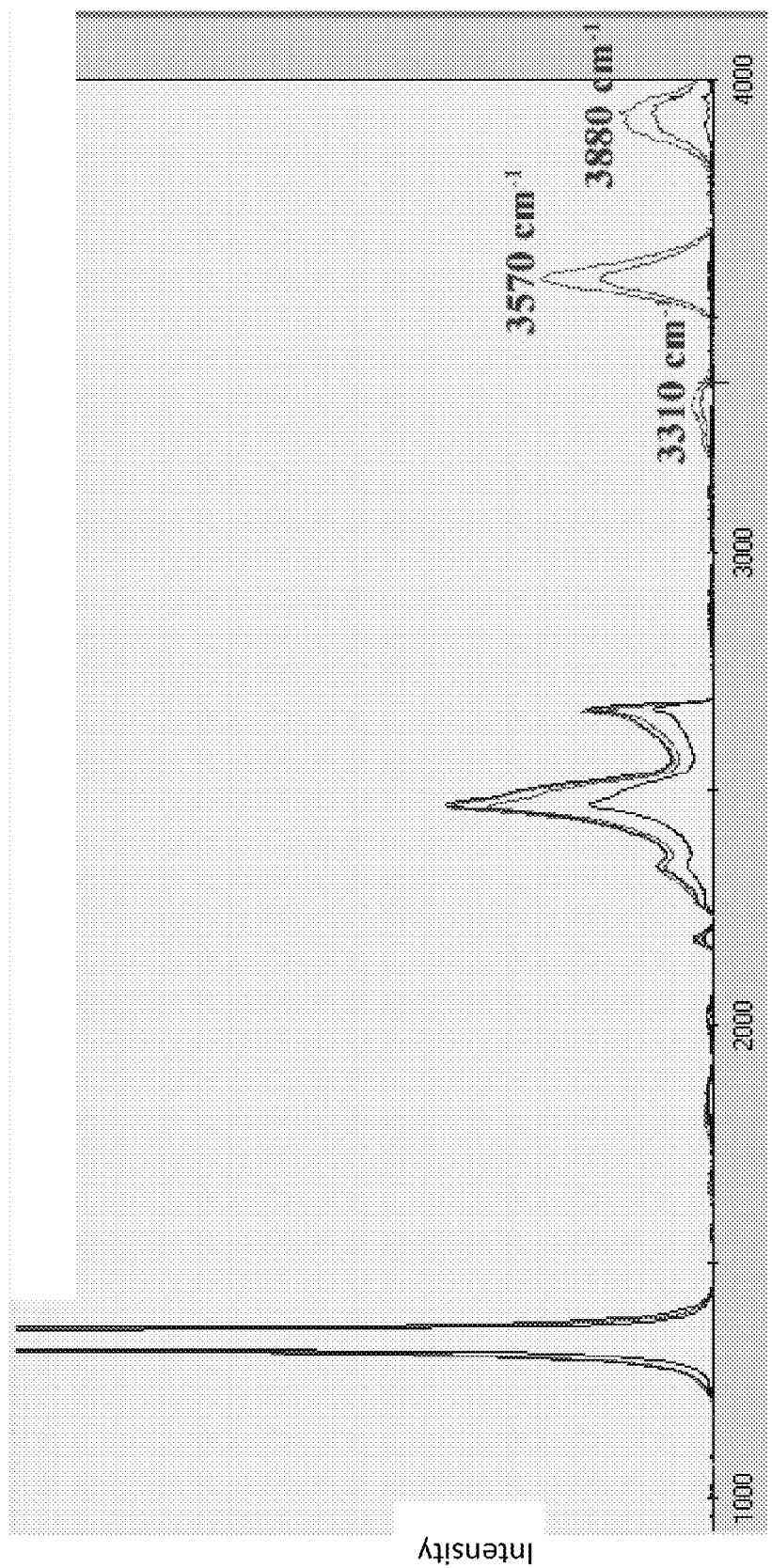

In addition, further place two outputs from each of the natural, CVD and HPHT samples under stacked comparative analysis (see FIG. 5-1~5-2). One can easily observe the differences between them with the evident characteristic Raman peaks; with these strong differences between the characteristics peaks, the method of the present invention can resolve that this described Raman identification technique is fast, accurate, and is entirely different from the traditional approach.

Figure 6:
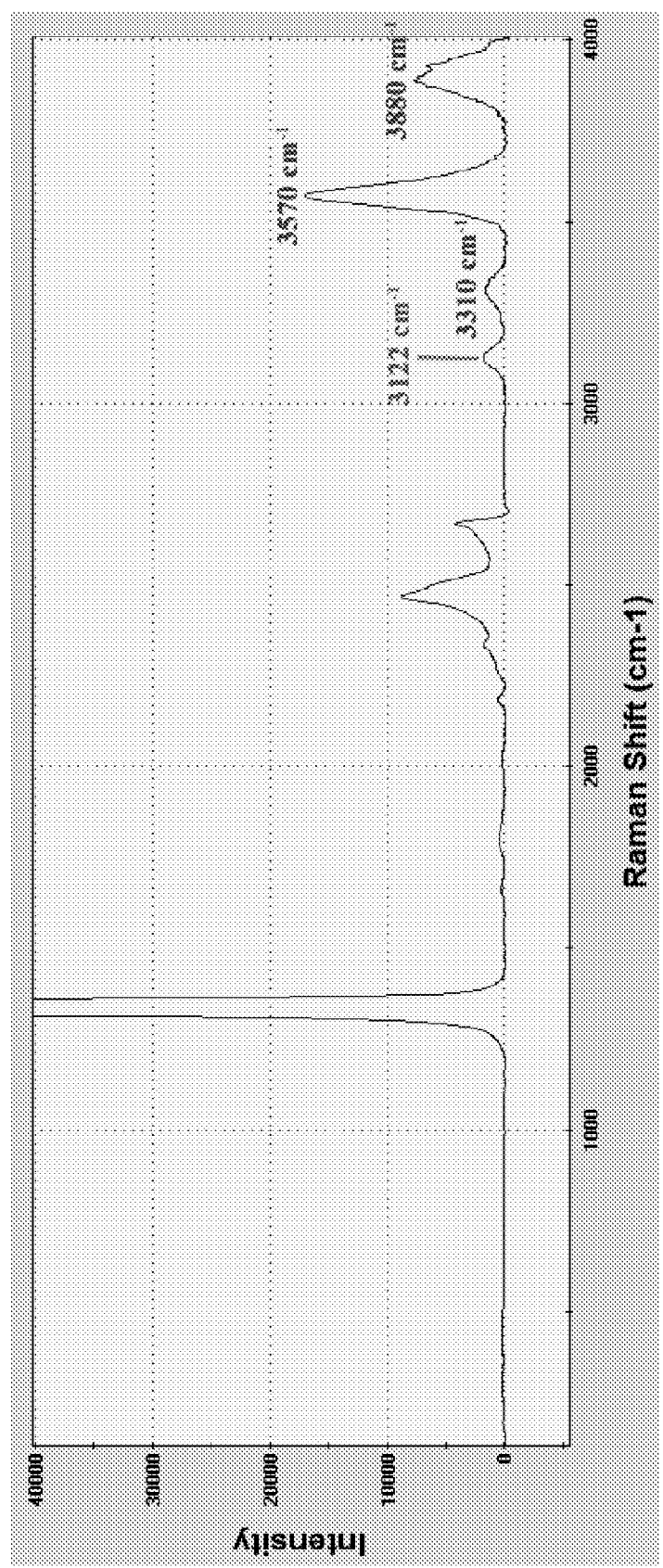
FIG. 6 shows Raman spectra of HPHT treated natural diamond.

Most of the natural diamonds which underwent HPHT treatment for color adjustment, will find in addition to the third-order natural diamond Raman peak at 3310 $cm^{-1}$, also exhibit 3570 $cm^{-1}$, and 3880 $cm^{-1}$ responses between the 3000 to 4000 wave numbers. It will also carry a 3122 $cm^{-1}$ characteristic fluorescence peaks, of which the position is much similar to a lattice defects in CVD diamonds (see FIG. 6). This is the result from the manufacturing process that the CVD diamond also typically undergo HPHT treatment to improve its color, so its lattice defect developing fluorescent peak (3122 $cm^{-1}$) will be similar to the response from a HPHT treated natural diamonds. Because influenced by stress effect, the third-order natural diamond Raman peak will shift left a little after treated by HPHT.

Using Raman analyzer as a quick screening tool to identify natural diamonds and synthetic diamonds will give a strong competitive advantage over other comparable technologies. However, in the past the instrument function has technical limitations, especially the lack of sensitivity, so it was not likely to display the characteristic peaks necessary for modern identification. Relevant research literature is thus lacking (especially in diamond's third-order analysis), thus making the laboratory procedure difficult to evolve into a technical solution. The method of the present invention highlights the following: as long as the Raman analyzer is equipped with adequate performance, it is very quick and simple to determine the differences between the natural and synthetic diamonds. After all, all optimization techniques will leave noticeable characteristics through the analysis of micro-substances; on the prerequisite that the Raman analyzer high enough "sensitivity".

Accordingly, when Raman analyzer is used with the method of the present invention to obtain enough scientific data so as to produce consistency and reproducibility of the result, there is no need to seek for other instruments for duplicated testing. Moreover, Raman analysis is simple and fast, and is able to perform "live rapid screening" without damaging the test samples, and the analytical outcome is fully supported by scientific data—these are the advantages of Raman analysis by means of the method of the present invention.

It is understood that the invention may be embodied in other forms within the scope of the claims. Thus the present examples and embodiments are to be considered in all respects as illustrative, and not restrictive, of the invention defined by the claims.

What is claimed is:

1. A method of rapid identification of natural and synthetic diamonds using a third-order Raman spectra, the method comprising steps of:
    providing a Raman analyzer operating with a laser power at 50 mW, a laser beam of wavelength 532 nm, and spectral collection time of 0.1 seconds at an average of 20 times, for an average detection of surfaces of diamonds;
    utilizing a large spot scanning probe for sample screening and obtaining wave number and intensity of the diamonds;
    the wave number and intensity being automatically corrected via a software and a background fluorescence being masked automatically;
    a spectral range of the Raman analyzer used for data acquisition set to be 100-4200 $cm^{-1}$ in order to facilitate a Raman spectrum with the correct strength and a flat baseline; and
    the spectrum being further normalized to identify treated samples with a third-order spectrum.

2. The method of claim 1, wherein spectra of the natural diamonds are between 3000~4000 $cm^{-1}$ wavenumber of the third-order spectrum positioned at 3310 $cm^{-1}$, 3570 $cm^{-1}$, and 3880 $cm^{-1}$ as three main Raman peaks.

3. The method of claim 1, wherein the synthetic diamonds produced by chemical vapor deposition (CVD) exhibits two fluorescence peaks close at 3120 $cm^{-1}$ and 3620 $cm^{-1}$.

4. The method of claim 1, wherein the synthetic diamonds produced by high pressure high temperature (HPHT) do not carry any fluorescent or Raman peaks.

* * * * *